US009238580B2

(12) United States Patent
Alagarsamy et al.

(10) Patent No.: US 9,238,580 B2
(45) Date of Patent: Jan. 19, 2016

(54) SPREAD-SPECTRUM MEMS SELF-TEST SYSTEM AND METHOD

(71) Applicant: Analog Devices Global, Hamilton (BM)

(72) Inventors: Kamatchi Saravanan Alagarsamy, Bangalore (IN); William A. Clark, Winchester, MA (US); Jishnu Choyi, Kerala (IN); James M. Lee, Northborough, MA (US); Vikas Choudhary, Bangalaore (IN)

(73) Assignee: Analog Devices Global, Hamilton (BM)

( * ) Notice: Subject to any disclaimer, the term of this patent is extended or adjusted under 35 U.S.C. 154(b) by 349 days.

(21) Appl. No.: 13/793,574

(22) Filed: Mar. 11, 2013

(65) Prior Publication Data

US 2014/0250969 A1    Sep. 11, 2014

(51) Int. Cl.
*B81B 7/02* (2006.01)
*G01N 35/00* (2006.01)
*B81B 7/00* (2006.01)
*B81C 99/00* (2010.01)

(52) U.S. Cl.
CPC . *B81B 7/02* (2013.01); *B81B 7/008* (2013.01); *B81C 99/005* (2013.01); *G01N 35/00712* (2013.01)

(58) Field of Classification Search
CPC .............. G01N 2035/00683; G01N 35/00712; G01P 2015/0868
See application file for complete search history.

(56) References Cited

U.S. PATENT DOCUMENTS

| 5,506,454 | A | 4/1996 | Hanzawa et al. ............. 307/10.1 |
| 5,900,529 | A | 5/1999 | Hanisko et al. ................ 73/1.38 |
| 7,250,772 | B2 | 7/2007 | Furse et al. .................... 324/534 |
| 7,622,931 | B2 | 11/2009 | Wu et al. ........................ 324/534 |
| 2009/0241634 | A1 | 10/2009 | Acar ............................... 73/1.79 |
| 2010/0145660 | A1* | 6/2010 | Lang et al. ..................... 702/193 |
| 2011/0313691 | A1 | 12/2011 | Dobson et al. .................. 702/58 |

OTHER PUBLICATIONS

Deb et al. "Built-In Self Test of CMOS-MEMS Accelerometers", IEEE—ITC International Test Conference, Paper 37.3, pp. 1075-1084, Oct. 2002.
Lelong et al. "On Line Wire Diagnosis by Modified Spread Spectrum Time Domain Reflectometry", PIERS Proceedings, Cambridge, US, pp. 182-186, Jul. 2-6, 2008.
Rufer et al. "On-chip pseudorandom MEMS testing", TIMA Lab. Research Reports, ISSN 1292-1862, 7 pages, May 2003.
Smith et al., "Fault Location on Aircraft Wiring Using Spread Spectrum Time Doman Reflectometry", Draft Paper under review for IEEE Transactions on Electromagnetic Compatibility (T-EMC) Journal, 22 pages, Oct. 27, 2003.

(Continued)

*Primary Examiner* — Paul West
(74) *Attorney, Agent, or Firm* — Sunstein Kann Murphy & Timbers LLP

(57) ABSTRACT

A MEMS sensor includes a micro-electromechanical structure, a detection circuit, and a self-test circuit to test the health of the MEMS sensor during runtime operations. The self-test circuit is configured to inject into the micro-electromechanical structure a plurality of injected test signals that are broadband frequency-varying frequency signals, which are based on spread spectrum based modulation. The injected test signals may a magnitude that is below an observable threshold of the sensor signal as well as a test-signal bandwidth that overlaps with a substantial portion of the sensor bandwidth, including the stimulus of interest.

20 Claims, 13 Drawing Sheets

(56) References Cited

OTHER PUBLICATIONS

Xie et al., "Fabrication, Characterization, and Analysis of a DRIE CMOS-MEMS Gyroscope", IEEE Sensors Journal, vol. 3, No. 5, pp. 622-631, dated Oct. 2003.
Japanese Patent Office, English Retranslation of the Claims—Application No. 2014-44971, 10 pages, dated Mar. 7, 2014.
Yamamoto, Email from Yamamoto to Klayman, dated Feb. 2, 2015 summarizing the Office Action for Application No. 2014-44971 received on Jan. 22, 2015, 2 pages.
Yamamoto, An English translation of amended claims as filed with the JPO—Application No. 2014-44971, 10 pages, dated Feb. 17, 2015.
Korean Intellectual Property Office, Office Action—Notice of Preliminary Rejection, Application No. 10-2014-0027955, 3 pages, dated Jun. 10, 2015 (English translation).
Kim & Chang, Response to the Rejection—Application No. 10-2014-0027955, 3 pages, dated Jul. 14, 2015, (English translation).
Kim & Chang, Proposed Claim Amendment—Application No. 10-2014-0027955, 6 pages, dated Jul. 14, 2015 (English translation).

* cited by examiner

SPREAD-SPECTRUM MEMS SELF-TEST SYSTEM AND METHOD

FIELD OF THE INVENTION

The present invention relates generally to a micro-electromechanical system (MEMS) device, more particularly a MEMS sensor having spread spectrum modulation self-testing capabilities.

BACKGROUND OF THE INVENTION

Inertial-based MEMS sensors, such as MEMS gyroscopes and accelerometers, are generally being used in greater quantities and in greater numbers of controls applications in automotive and vehicle systems. These applications may include, for example, usage in electronic stability controls (ESC), anti-lock braking systems (ABS), and supplemental restraint systems (SRS). Such sensors are also being used in various other applications, for example, in medical systems, such as in mechanized prostheses. In these and other MEMS applications, self-testing capability (also referred to as health monitoring) may be a beneficial if not a necessary feature to ensure that the MEMS sensor is operating properly within the application.

To ensure the proper operations of the MEMS sensor, those in the art have developed MEMS sensors with in-the-field self-testing capability. This self-test function generally entails injecting a known stimulus into the micro-electromechanical structure of a MEMS sensor during the initialization or startup operation of the sensor. As such, such self-test function may not observe a fault during the runtime operation.

Those in the art also have employed test function during the runtime operation of the sensor. The test stimulus of such runtime operation typically consists of an impulse response or a waveform that is applied outside the bandwidth or frequency of the stimulus of interest, which is generally a physical attribute intended to be observed by the MEMS sensors. As such, the test may provide an incomplete test of the MEMS sensor, as a portion of the potential bandwidth for measurement may be allotted for the testing function. Additionally, since the test is applied to a limited frequency range, the self-test function may, for example, fail to detect a defect that manifests in a specific frequency range. In particular, MEMS gyroscopes employed in ESC systems, for example, have been found to have certain linear and torsional vibration frequency that may not be measured concurrently with the operation of the self-test function.

Moreover, the bandwidth of a MEMS sensor is generally constrained by the design limitations and material properties of the micro-electromechanical structures. Thus, increasing the bandwidth of the MEMS sensor may require a redesign of the sensor, which may not be cost effective or possible.

SUMMARY OF EXEMPLARY EMBODIMENTS

In one embodiment there is provided a MEMS sensor having a runtime self-test circuit, wherein the MEMS sensor comprises a micro-electromechanical device that outputs, during runtime operation, a device output signal; a detection circuit configured to detect, during the runtime operation of the micro-electromechanical device, a stimulus produced by the micro-electromechanical system in a sensor bandwidth of the device output signal, the stimulus having a magnitude above a predetermined detection threshold of the detection circuit, the detection circuit further configured to produce a sensor output signal based on the detected stimulus; and a self-test circuit configured to (1) inject, during the runtime operation of the micro-electromechanical device, a self-test signal into a signal path of the micro-electromechanical device including a MEMS structure involved with generation of the stimulus in the sensor bandwidth of the device output signal, wherein the self-test signal is a spread-spectrum signal having a test-signal bandwidth that overlaps at least a portion of the sensor bandwidth; (2) detect a test signal component in the test-signal bandwidth of the device output signal based on a reference test signal corresponding to the injected self-test signal, the test signal component have a magnitude below the detection threshold of the detection circuit; and (3) produce a test output signal indicating a status for the micro-electromechanical system based on the test signal component and the reference test signal.

In another embodiment there is provided a self-test circuit for a micro-electromechanical system that outputs, during runtime operation, a device output signal including a stimulus in a sensor bandwidth of the device output signal, the stimulus having a magnitude above a predetermined detection threshold. The self-test circuit comprises a self-test signal generator configured to inject, during runtime operation of the micro-electromechanical device, a self-test signal into a signal path of the micro-electromechanical device including a MEMS structure involved with generation of the stimulus in a sensor bandwidth of the device output signal, wherein the self-test signal is a spread-spectrum signal having a test-signal bandwidth that overlaps at least a portion of the sensor bandwidth; a self-test signal detector configured to detect a test signal component in the test-signal bandwidth of the device output signal based on a reference test signal corresponding to the injected self-test signal, the test signal component have a magnitude below the detection threshold of the detection circuit; and a controller configured to produce a test output signal based on the detected test signal component.

In various alternative embodiments, the self-test circuit may be configured to continuously inject the self-test signal into the micro-electromechanical device during the runtime operation of the micro-electromechanical device. The self-test circuit may include a pseudo-random number sequence source configured to provide a pseudo-random number sequence and a modulation circuit configured to modulate the pseudo-random number sequence and a self-test magnitude reference to produce a modulated signal and to inject the modulated signal into the micro-electromechanical device. The self-test magnitude reference may be a constant direct-current (DC) source. The pseudo-random number sequence source may comprise a pseudo-random number generator. The pseudo-random number sequence source may comprises a memory in which is stored the pseudo-random number sequence. The bandwidth of the self-test signal may be equal to the sensor bandwidth, less than the sensor bandwidth, or greater than the sensor bandwidth. The bandwidth of the self-test signal may extend below the sensor bandwidth and/or may extend above the sensor bandwidth. The self-test circuit may also include a demodulation circuit configured to detect the test signal component by demodulating the device output signal with the reference test signal in-phase with test signal component. The self-test circuit may include a low-pass filter to extract the test signal component from the device output signal. The self-test circuit may include a delay circuit to produce the reference test signal in-phase with the test signal component. The self-test circuit may include a memory to provide the reference test signal. The demodulation circuit may comprise a multiplier to combine the test signal component with the in-phase reference test signal.

In certain embodiments, the self-test circuit may be configured to detect the test signal component in the test-signal bandwidth of the device output by (i) correlating the sensor signal with the pseudo-random number sequence in phase with the sensor signal to produce a correlation signal and (ii) comparing the correlation signal to at least one of a pre-defined correlation threshold or a pre-defined signal energy threshold. The pre-defined energy threshold may be established based on the relationship fc*STM2, wherein fc is a frequency value of the injected self-test test signal and STM is an average power of a period spread of the injected self-test signal.

In any of the above embodiments, the self-test circuit may be configured to inject the self-test signal according to at least one of a frequency-hopping spread spectrum modulation, a direct-sequence spread spectrum (DSSS) modulation, a time-hopping spread spectrum modulation, or a chirp spread spectrum modulation. The micro-electromechanical device may include an inertial sensor, a sound sensor, a pressure sensor, and/or other MEMS sensor or device.

In another embodiment there is provided a method of evaluating the status of a MEMS sensor during runtime, the MEMS sensor having a micro-electromechanical device that outputs, during a runtime operation, a device output signal, the MEMS sensor further having a detection circuit configured to detect, during the runtime operation of the micro-electromechanical device, a stimulus produced by the micro-electromechanical system in a sensor bandwidth of the device output signal, the stimulus having a magnitude above a pre-determined detection threshold of the detection circuit, the detection circuit further configured to produce a sensor output signal based on the detected stimulus. The method involves injecting, during runtime operation of the micro-electromechanical device, a self-test signal into a signal path of the micro-electromechanical device including a MEMS structure involved with generation of a stimulus in a sensor bandwidth of a device output signal, wherein the self-test signal is a spread-spectrum signal having a test-signal bandwidth that overlaps at least a portion of the sensor bandwidth; detecting a test signal component in the test-signal bandwidth of the device output signal based on a reference test signal corresponding to the injected self-test signal, the test signal component have a magnitude below the detection threshold of the detection circuit; and producing a test output signal based on the detected test signal component.

Additional embodiments may be disclosed and claimed.

BRIEF DESCRIPTION OF THE DRAWINGS

The foregoing features of embodiments will be more readily understood by reference to the following detailed description, taken with reference to the accompanying drawings, in which.

It should be noted that the foregoing figures and the elements depicted therein are not necessarily drawn to consistent scale or to any scale. Unless the context otherwise suggests, like elements are indicated by like numerals.

DETAILED DESCRIPTION OF SPECIFIC EMBODIMENTS

Figure 1:
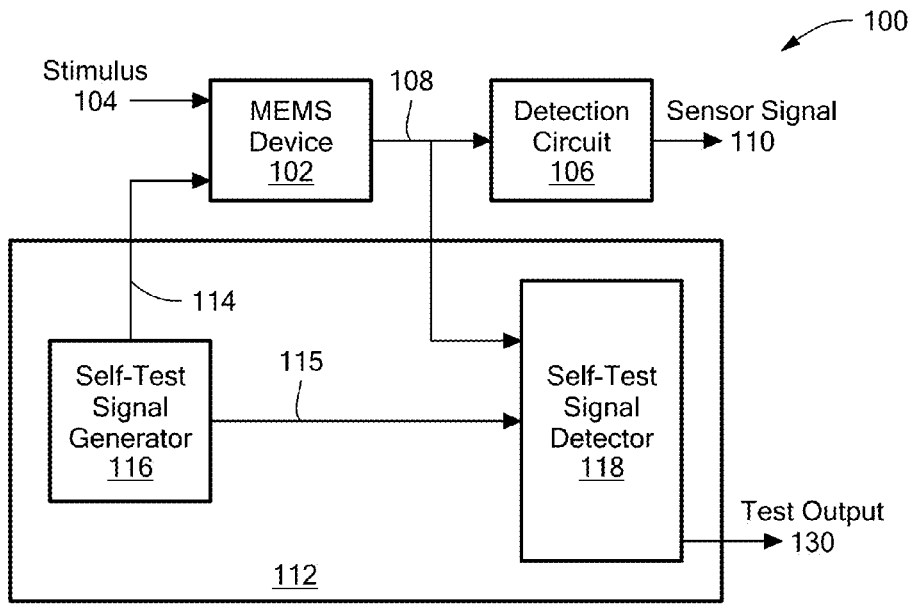
FIG. 1 schematically shows an in-field self-test MEMS sensor according to an illustrative embodiment.

As used herein, the term "self-test" refers to injecting a known test stimulus into a sensor, e.g., via an internal testing component of the sensor, and then measuring and analyzing a corresponding output to determine whether the sensor is operating within a specified set of operations (i.e., working/not working or passed/failed). The term "self-test" is interchangeably used herein with "health monitoring."

As used herein, the term "runtime" refers to an intended mode of operation. In the context of sensors, for example, the runtime operation includes a period of sensor operation when the sensor is sensing the stimulus of interest.

As user herein, the term "continuous" refers to an on-going operation and/or without interruption.

There is a benefit in having a MEMS sensor with continuous self-testing capabilities that does not have to trade-off its effective sensing bandwidth with the self-test function. There is also a benefit in having a MEMS sensor that operates across a greater region of or across the entire bandwidth range of the sensor.

In exemplary embodiments, a MEMS sensor includes a self-test circuit that performs self-testing operations within a portion of the sensing bandwidth of the sensor, including up to the entire range thereof. The testing further provides a test stimulus having a magnitude below an observable threshold of the sensor. As such, the testing does not interfere with the runtime measurement and may be performed concurrently (e.g., continuously) during the runtime operation of the sensor while not requiring a dedicated portion of the bandwidth of the MEMS sensor to operate. Thus, the exemplary embodiment may provide a comprehensive testing scheme in evaluating up to the entire bandwidth of the sensor. In addition to a more comprehensive test, embodiments generally provide an increased sensing bandwidth for a given mechanical design.

To provide such a testing function, the exemplary embodiments employ a spread spectrum test stimulus. Although those in the art have employed spread spectrum modulation in other testing methodologies, such as in reflectometry for the testing of faulty cables, such methodologies are non-analogous art due to a different underlying mode of operation. For example, rather than merely characterizing impedance of a solid static structure as with reflectometry, testing of a MEMS sensor generally entails characterizing the dynamic operations of intricate components in the sensor.

Herein, the inventor has recognized that the self-testing of MEMS sensors can be accomplished using spread spectrum based modulation. Specifically, the inventors have discovered that a test signal may be injected at a signal level below an observable threshold of the MEMS sensor because the coding modulation may provide sufficient signal for the test signal to be detected. In conjunction therewith, the inventor inferred that the coupling between the dynamic operation of the micro-electromechanical structure and the injected test signal may provide information about the micro-electromechanical structure, including, for example, that the structure is or is not operating as intended. Specifically, an inference may be made that the structure of the MEMS sensor when operating as intended allows for the modulated test signal to be retrieved, whereas a faulty structure would distort or impede the modulated test signal.

Put differently, exemplary embodiments employ a coding modulation that primarily operates in an information domain that is weakly linked to the physical domain. The exemplary embodiments may advantageously use this relationship by using a weak stimulus in the physical domain, but one which is strong in the information domain. As such, the stimulus may be configured to not be observable by the sensor in the physical domain. However, the strong information component that is weakly coupled to the physical domain may nevertheless be amplified to allow information to be transmitted therethrough.

To do so, exemplary embodiments may, for example, inject multitudes of weak electrical signal into the physical structure of the MEMS sensor. These weak electrical signals individually produce mechanical responses that are not generally observable by the sensor to affect observation of the stimulus of interest. However, when the multitudes of signals are evaluated together over a period time, a correlation develops among the injected signals. This correlation forms the basis of the inference. Specifically, if the physical structure is operating as intended, a certain degree of correlation is expected. And, when the physical structure is not operating properly, a lesser correlation may form as the defect in the physical structure (e.g., mechanical and/or electrical structure) would affect the responses produced by the injected test signal. As a result, exemplary embodiments may employ any of various types of spread-spectrum-based modulation.

FIG. 1 is a schematic block diagram showing a MEMS sensor 100 having a spread-spectrum-based runtime self-test circuit such as for continuous self-test, according to one illustrative embodiment. The MEMS sensor 100 includes a MEMS device 102 that is configured to respond, or is sensitive, to an intended stimulus 104 (also referred herein as a stimulus of interest) corresponding to a physical attribute such as, for example, a change in inertia, acceleration, mechanical deformation, sound waves, pressure, centrifugal force, gravitational force, electric force, magnetic force, thermal gradient, or electromagnetic force. The MEMS device 102 may be configured to sense the physical attribute, e.g., exhibited as a capacitance, inductance, or resistance value or a change thereof, and generate a device output signal 108 corresponding thereto. For example, the MEMS device 102 may have a movable mass capacitively coupled to a sense electrode that generate a varying device output signal 108 based on the position of the movable mass. The device output signal 108 may be generated in other ways using other types of MEMS structures (e.g., capacitively coupled, mechanically coupled, piezoelectric, etc.) in a wide variety of MEMS device types (e.g., gyroscopes, accelerometers, microphones, switches, etc.).

The MEMS sensor 100 further includes a detection circuit 106 that operatively couples with the MEMS device 102 to sense, via the device output signal 108, a physical attribute corresponding to a stimulus 104 exerted on the MEMS device 102. During the runtime operation of the MEMS sensor 100, the detection circuit 106 processes the device output signal 108 to produce a sensor output signal 110 corresponding to the stimulus 104 (e.g., a sensor output signal indicative of rotation rate, linear acceleration, an acoustic signal, etc.), where the device output signal 108 has a bandwidth that includes the observable bandwidth of the MEMS device 102. As such, the device output signal 108 may have a bandwidth sufficient to observe the stimulus of interest.

The MEMS sensor 100 further includes a self-test circuit 112. The self-test circuit 112 is configured to inject a self-test signal 114 into at least one circuit path of the MEMS device 102 including a MEMS mechanical or electromechanical structure. The self-test circuit 112 may include a signal generator 116 that generates the self-test signal 114. The signal generator 116 may include a pseudo-random number sequence generator that generates a binary sequence (e.g., a sequence of '0' and '1') having broad frequency components. For example, a pseudo-random number sequence generator may include a linear feedback shift register (LFSR). The signal generator 116 may generate a frequency-varying signal having any of various types of distributions, such as, for example, a Gaussian distribution (i.e., normal), an asymmetric distribution (i.e., skewed), or a uniform distribution. The bandwidth of the self-test signal 114 may correspond to the distribution of the frequency of the pseudo-random number sequence; thus the distribution may be configured to cover a specific frequency range. The pseudo-random number sequence may be generated during runtime operations or may be stored to be retrieved during runtime operation. Herein, the term "pseudo-random" generally refers to being related to or having been generated by a definite nonrandom computational process. The pseudo-random number sequence may be used as, or may form the basis of, the self-test signal 114.

As such, the self-test signal 114 may be a broad-band frequency-varying signal having a bandwidth that overlaps with at least a portion of the sensor bandwidth up to and including the entire bandwidth and may have a bandwidth that extends above and/or below the sensor bandwidth (e.g., the self-test signal bandwidth may be wider than the sensor bandwidth). Herein, the term "broad-band" refers to the wide bandwidth characteristic of the signal. As such, the self-test signal 114 may vary according to any of various types of spread spectrum techniques, such as, for example, frequency-hopping spread spectrum (FHSS), direct-sequence spread spectrum (DSSS), time-hopping spread spectrum (THSS), or chirp spread spectrum (CSS). The self-test signal 114 may further have a magnitude below a signal level observable by the detection circuit 106, including, for example, the noise-floor thereof.

The self-test circuit 112 may inject the self-test signal 114 according to any of various methods. For example, in certain MEMS sensors, the MEMS sensor includes a driver circuit that places a fixed or varying electrical signal on a MEMS structure or MEMS circuit path (e.g., a resonator, accelerometer proof mass, microphone diaphragm, drive electrodes, sense electrodes, etc.). As such, the self-test circuit 112 may, for example, inject the self-test signal 114 into the driver circuit of the MEMS sensor. Alternatively, the self-test circuit 112 may include a secondary driver circuit to operate independent of or dependent with the driver circuit, where the secondary driver circuit applies the self-test signal 114 to the MEMS device 102.

The self-test circuit 112 may include a self-test signal detector 118 configured to detect spread-spectrum test signal components in the device output signal 108 based on a reference test signal 115. The reference test signal 115 may be the self-test signal 114 or another signal, such as, for example, a delayed version of the self-test signal 114, an expected output characteristic of the signal such as a power or correlation value, or other reference signal.

To do the detection, the self-test signal detector 118 may receive the reference test signal 115 and may compare the reference test signal 115 with, or operate on, the test signal components of device sensor signal 108. For example, the self-test signal detector 118 may include a demodulation circuit (not shown) having a multiplier to demodulate the test signal components with the reference test signal 115. The reference self-test signal 115 may be delayed to synchronize the two signals. As such, the self-test signal detector 118 may include a delay filter having a delay constant corresponding to the signal propagation time through the MEMS device 102. Alternatively to a demodulation circuit, the self-test signal detector 118 may employ various signal or power correlation filters to determine the correlation between the test signal components of the device sensor signal 108 and the self-test signal 114. The self-test circuit 112 may produce a test output 130 providing a status indication for the MEMS sensor 100, e.g., a pass/fail status or a degree of confidence or operation based on the amount of correlation between the test signal components and the reference test signal.

The self-test circuit 112 may continuously inject the self-test signal 114. Alternatively, the injection may be periodic or based on a trigger condition.

Figure 2:
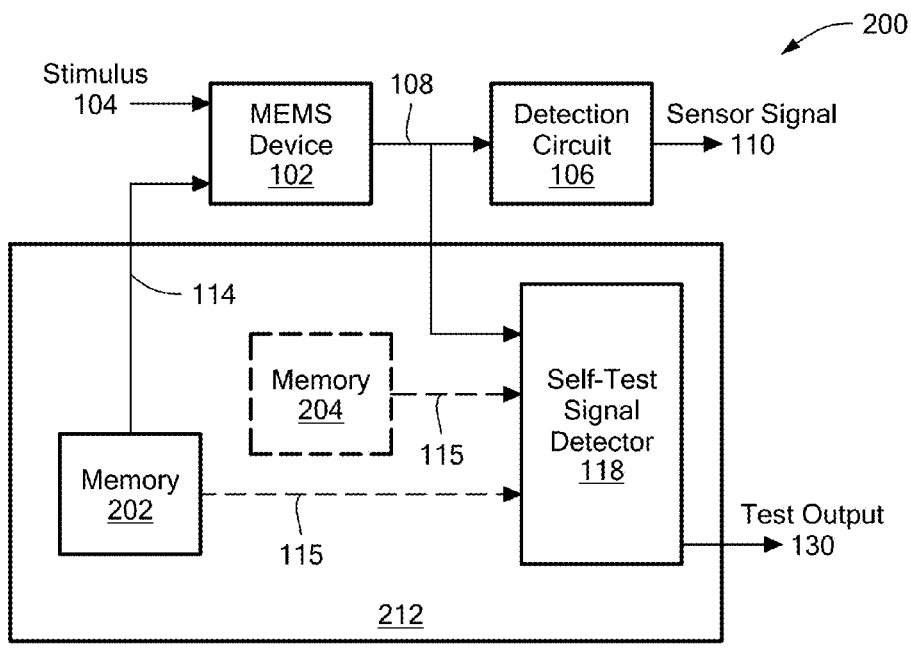
FIG. 2 schematically shows a continuous self-test circuit of a MEMS sensor according to an alternate embodiment.

As stated above, the pseudo-random number sequence may be generated during runtime operations or may be stored to be retrieved during runtime operation. FIG. 2 is a schematic block diagram showing a MEMS sensor 200 having a spread-spectrum-based runtime self-test circuit such as for continuous self-test, according to another illustrative embodiment. Here, rather than generating a pseudo-random number sequence, the self-test circuit 212 includes a memory module 202 having a pseudo-random number sequence stored therein. The self-test circuit 212 may retrieve the stored pseudo-random number sequence from the memory module 202 and use the stored number sequence for generating the self-test signal 114.

To detect the detected test signal, the self-test circuit 212 may employ a self-test signal detector 118 substantially as described above. For example, the self-test signal detector 118 may retrieve the reference test signal 115 from the memory module 202. Alternatively, the self-test circuit 212 may include a second memory module 204 having stored therein a reference test signal 115. As such, the self-test signal detector 118 may obtain the reference test signal 115 from the second memory module 204.

Figure 3:
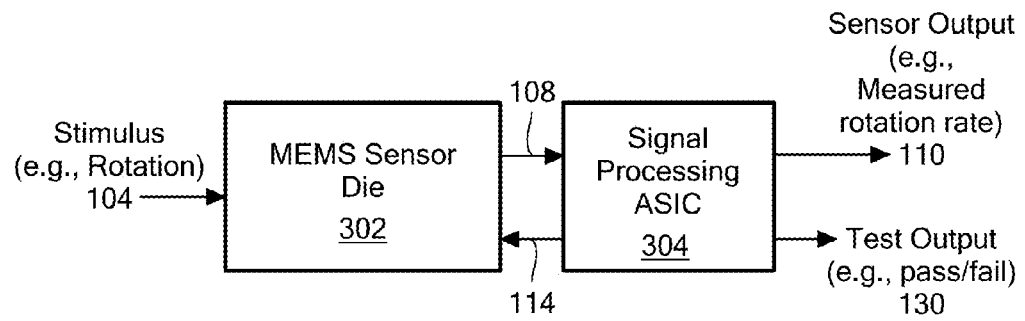
FIG. 3 schematically shows a MEMS system according to an embodiment.

FIG. 3 schematically shows an implementation of a MEMS sensor 100 according to an illustrative embodiment. The sensor includes a MEMS sensor die 302 and a signal processing application-specific integrated circuit (ASIC) 304. The MEMS sensor die 302 may be configured to observe a stimulus 104, such as, for example, a rate of rotation or acceleration, a sound source, etc. The MEMS sensor die 302 may include various mechanical and electromechanical structures (e.g., resonator, proof mass, microphone diaphragm, drive electrodes, sense electrodes, etc.).

The signal processing ASIC 304 may include the detection circuit 106 and the self-test circuit 112. The signal processing ASIC 304 produces the sensor output 110, such as, for example, a measured rate of rotation or acceleration, an audio output signal, etc. The signal processing ASIC 304 also produces a test output 130. The test output may indicate a pass or a fail status of the MEMS sensor die 302. The signal processing ASIC 304 may provide the self-test signal 114 to the MEMS sensor die 302 and receive the device output signal 108. The MEMS sensor die 302 and signal processing ASIC 304 may be implemented on a single die.

Figure 4A:
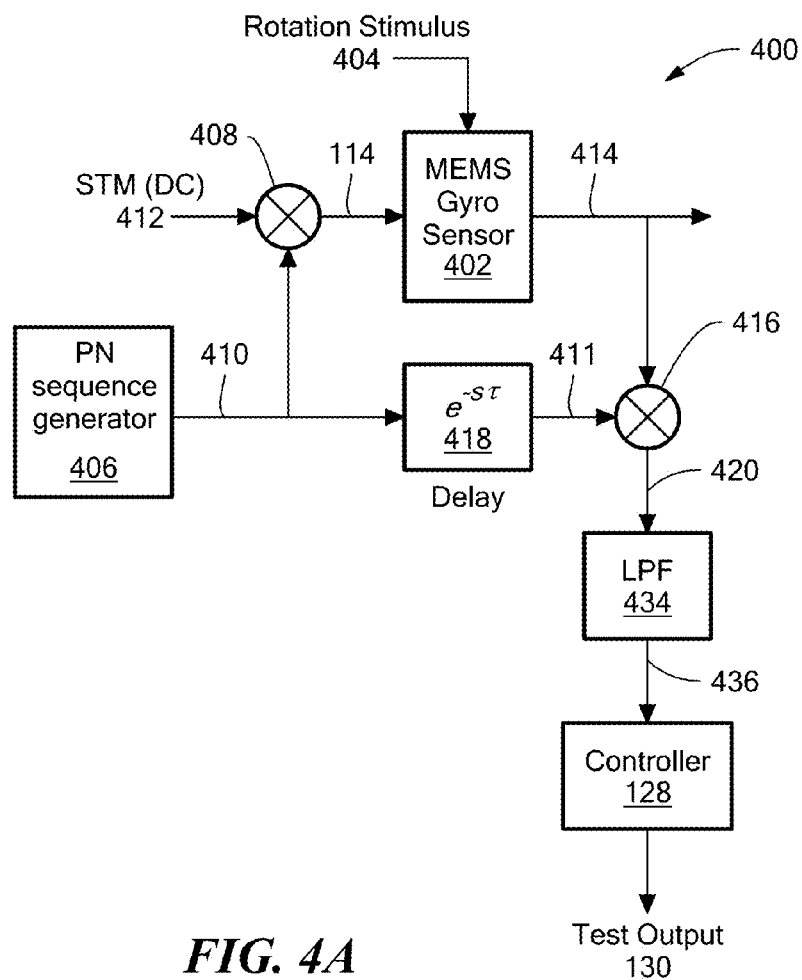
FIG. 4A schematically shows a MEMS system of FIG. 3 according to an embodiment.

FIG. 4A schematically shows a MEMS-ASIC system of FIG. 3 according to an illustrative embodiment. FIG. 4A is described in conjunction with FIG. 4B, which illustrates example frequency characteristics of self-test signals in the MEMS-ASIC system according to the illustrative embodiment. In this example, the MEMS-ASIC system 400 includes a MEMS inertial sensor, configured with a MEMS gyroscope sensor 402. In the sensor 402, a reference vibration is applied to a micro-mechanical structure therein, and a measurable stimulus corresponding to a rotation stimulus 404 is produced through the Coriolis effect when the sensor is rotated. The rotation stimulus 404 may be expressed as x(t) where t corresponds to time. The MEMS gyroscope sensor 402 may include other circuits, such as a detection circuit to detect the rotation stimulus 404.

The MEMS-ASIC system 400 may include a self-test signal injection portion that may include a pseudo-number generator 406 and a multiplier 408. The pseudo-number generator 406 may generate a pseudo-number sequence 410. The multiplier 408 may modulate the pseudo-number sequence 410 with a self-test magnitude reference 412 to produce the self-test signal 114 to be injected into the sensor 402. The self-test magnitude reference 412 may be a constant direct-current (DC) source.

The self-test signal 114 may be expressed as s(t), as shown in Equation 1. The self-test signal 114, s(t), may be a multiplication between the self-test magnitude reference 412, expressed as STM(t), and the pseudo-number sequence 410, expressed as PN(t).

$$s(t)=STM(t)*PN(t) \quad \text{(Equation 1)}$$

The self-test signal 114, s(t), may have a bandwidth that is spread over the bandwidth BW of the MEMS gyroscope sensor 402. The pseudo-random number sequence generator 406 may generate the pseudo-number sequence 410 as a binary sequence between −1 and +1 (or 0 and 1) with a length L and a bandwidth of BW. The bit rate of the pseudo-number sequence 410 may establish the bit rate of the self-test signal 114. The bandwidth of the self-test signal 114 may be referred to as the chipping frequency.

The self-test magnitude reference 412, STM(t), may be regarded as a message signal in the context of a communication system and may be expressed as a scalar value STM when it is constant DC source. The STM or STM(t) is the reference test signal and thus forms the basis of a detected test signal. The MEMS gyroscope sensor 402 may provide output signal 414, d(t), which includes information component derived from the rotation stimulus 404 and the self-test signal 114, as shown in Equation 2.

$$d(t)=x(t)+STM*PN_{sensor}(t-\tau) \quad \text{(Equation 2)}$$

As indicated, x(t) is the rotation stimulus 404 (i.e., the stimulus of interest). The self-test signal 114, when propagated through the MEMS sensor, may be expressed as STM*$PN_{sensor}$(t–τ), where τ is the delay constant. The signal STM*$PN_{sensor}$(t–τ) may be regarded as an interference signal in a spread spectrum analysis.

The MEMS-ASIC system 400 may include a self-test signal detection portion to detect a detected test signal (i.e., STM(t) or STM) in the output signal 414. The self-test signal detection portion may include a multiplier 416 and a delay circuit 418. To do the detection, the self-test signal detection portion may use the multiplier 416 to multiply the output signal 414, d(t) and the pseudo-number sequence 411 in-phase therewith. The delay circuit 418 may delay the generated pseudo-random number sequence 410 with delay constant τ to generate the in-phase pseudo-number sequence 411, which is referred to as $PN_{ref}$(t–τ). The delay circuit 418 may have the form $e^{sτ}$. The output of the multiplier 420 may be expressed as y(t) as shown in Equation 3.

$$y(t)=d(t)*PN_{ref}(t-τ)$$ (Equation 3)

Equation 3 may be expanded with Equation 2 to provide Equation 4.

$$y(t)=[x(t)+STM*PN_{sensor}(t-τ)]*PN_{ref}(t-τ)$$ (Equation 4)

A property in pseudo-random number sequence operation is that multiplication of identical signal results in an identity function (i.e., a result of '1'). As such, if $PN_{sensor}$(t–τ) and $PN_{ref}$(t–τ) are identical (i.e., $PN_{sensor}$(t–τ)=$PN_{ref}$(t–τ)), the result of $PN_{sensor}$(t–τ)*$PN_{ref}$(t–τ) is "1". As such, y(t) may be expressed as y(t)=x(t)+STM.

However, where the $PN_{sensor}$(t–τ) and $PN_{ref}$(t–τ) are not identical (i.e., $PN_{sensor}$(t–τ)≠$PN_{ref}$(t–τ)), the result is a convolution of $PN_{sensor}$(t–τ) and $PN_{ref}$(t–τ). In such a scenario, y(t)=x(t)+STM*$PN_{sensor}$(t–τ)*$PN_{ref}$(t–τ).

In the context of testing, the MEMS-ASIC system 400 may infer that when $PN_{sensor}$(t–τ) and $PN_{ref}$(t–τ) are identical, then the MEMS gyroscope sensor 402 is operating as intended as it does not distort, impede, or alter the self-test signal 114 in propagating therethrough. Similarly, the MEMS-ASIC system 400 may infer that when $PN_{sensor}$(t–τ) and $PN_{ref}$(t–τ) are not identical, then the MEMS gyroscope sensor 402 is not operating as intended. Table 1 summarizes this test condition.

TABLE 1

| Condition of MEMS sensor | Inference of Test Condition | Output of Test (y(t)) |
|---|---|---|
| Operating as intended | $PN_{sensor}$(t – τ) = $PN_{ref}$(t – τ) | y(t) = x(t) + STM |
| Not operating as intended | $PN_{sensor}$(t – τ) ≠ $PN_{ref}$(t – τ) | y(t) = x(t) + STM * $PN_{sensor}$(t – τ) * $PN_{ref}$(t – τ). |

Figure 4B:
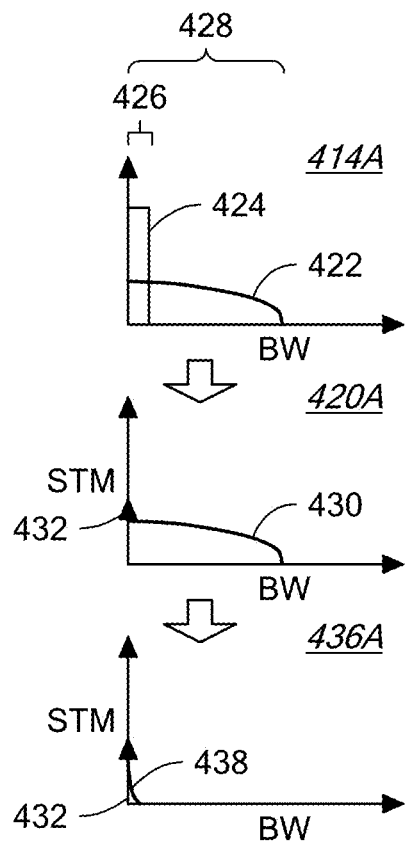
FIG. 4B illustrates frequency characteristics of the various self-test stimulus signals according to an embodiment.
Figure 4C:
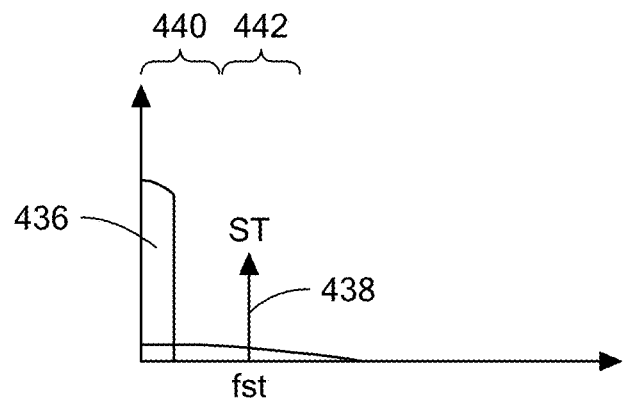
FIG. 4C shows frequency components of a sensor stimulus and self-test stimulus according to a conventional self-test system.

In plot 414A of FIG. 4B, the signal characteristics of the output signal 414 are shown. The x-axis is expressed in frequency and the y-axis is expressed in signal magnitude. As such, plot 414A shows a frequency distribution 422 of the rotation stimulus 404 and a frequency distribution 424 of the self-test magnitude reference 412. The rotation-stimulus frequency distribution 424 is shown as having bandwidth 426 while the STM frequency distribution 424 has a larger bandwidth 428. The bandwidth 426 represents the bandwidth of the MEMS-ASIC system 400 in observing or providing measurement for the rotation stimulus 404. The bandwidth 422 represents the bandwidth of the pseudo-random number sequence generated by the pseudo-random number sequence generator 406. As such, the test-signal bandwidth overlaps with a substantial portion of the sensor bandwidth, which includes the bandwidth of the stimulus of interest. Additionally, the detected test signal component has a magnitude below the observable threshold of the rotation-stimulus.

In plot 420A of FIG. 4B, the signal characteristics of the input and output of the multiplier 416 when the MEMS gyroscope sensor 402 is operating as intended. The plot 420A shows a frequency distribution 430 of the self-test signal 114 before and after transmission through the MEMS gyroscope sensor 402. Here, the self-test signal 114 has a bandwidth equivalent to the pseudo-random number sequence (e.g., $PN_{sensor}$(t–τ) and $PN_{ref}$(t–τ)). As such, since the MEMS gyroscope sensor 402 is operating as intended, the multiplication results in a dirac delta function 432 having a magnitude corresponding to the self-test magnitude reference 412, STM(t).

To extract the detected self-signal STM from the multiplier output signal 420, the MEMS-ASIC system 400 may include a low-pass filter 434 (referring back to FIG. 4A). The output of the low-pass filter 434 may be used as a basis for the test output 130 generated by a controller 128. As indicated, the test output 130 may provide a pass or fail status that indicates the proper or improper operation of the MEMS gyroscope sensor 402. The low-pass filter 434 may be any of various types of filters, including a cascaded integrator comb (CIC) filter.

In plot 436A of FIG. 4B, the signal characteristics of the output 436 of the low-pass filter 434 is shown. The plot 310A shows a filtered frequency distribution 438 of the rotation-stimulus frequency distribution 424 (as shown in plot 414A). Due to the filter, the rotation stimulus information has been substantially removed, and the detected test signal (i.e., the dirac delta function 432) remains. Here, the detected test signal may be regarded as the dirac delta function 432.

The MEMS-ASIC system 400 may include a controller 128 to provide the test output 130. The controller 128 may compare the detected test signal to the reference test signal. Here, the reference test signal may a dirac-delta function. As such, a presence of the dirac-delta function indicates a pass status and the lack of the function indicates a fail status.

Alternatively, the controller may compare the detected test signal to a reference signal that is a threshold (i.e., $C_{Threshold}$) or an equivalent thereto. As such, the pass condition may be $PN_{sensor}$(t–τ)*PN(t–τ)>$C_{Threshold}$, and the inverse is applied for the fail condition.

According to an alternative embodiment, rather than using a dirac-delta function as the reference test signal, the reference test signal may be an expected signal characteristic based of the self-test signal, including, for example, the average power.

For example, where the self-test magnitude reference 412 is a DC source STM, the average power ($Power_{average}$) may be expressed as $Power_{average}=f_c*STM^2$, where $f_c$ is the chipping frequency. A self-test signal may be expected to have all the power within a bandwidth BW, where a band-pass filter is employed in the signal path with bandwidth BW (e.g., f0/16). As such, when the length N of the pseudo-random number sequence is N=$2^r$–1 with chipping frequency $f_c$, the sequence repeats itself, in time domain, with a time period of T=N*(1/$f_c$). Thus, the frequency may be expressed as 1/T=$f_c$/N. As a result, the average power of the self-test signal with magnitude STM may be expressed as STM=Energy in T/T. Equation 4 shows the average power of this periodic varying frequency self-test signal $$Power_{average}=Energy\|T\|/T$$ (Equation 4)

Energy∥T∥ may be expressed as a sum of squared number sequence. Thus, the Power$_{average}$ may be expressed as follows in equation 5, where the number sequence x[n] is generated over the time period, T.

$$\text{Power}_{average} = \Sigma x[n]^2/T \quad \text{(Equation 5)}$$

Subsequently, equation 5 may be reduced as shown in Equation 6, where:

$$\text{Power}_{average} = N*STM^2/T = N*STM^2/(N/f_c) = f_c*STM^2 \quad \text{(Equation 6)}$$

Figure 5:
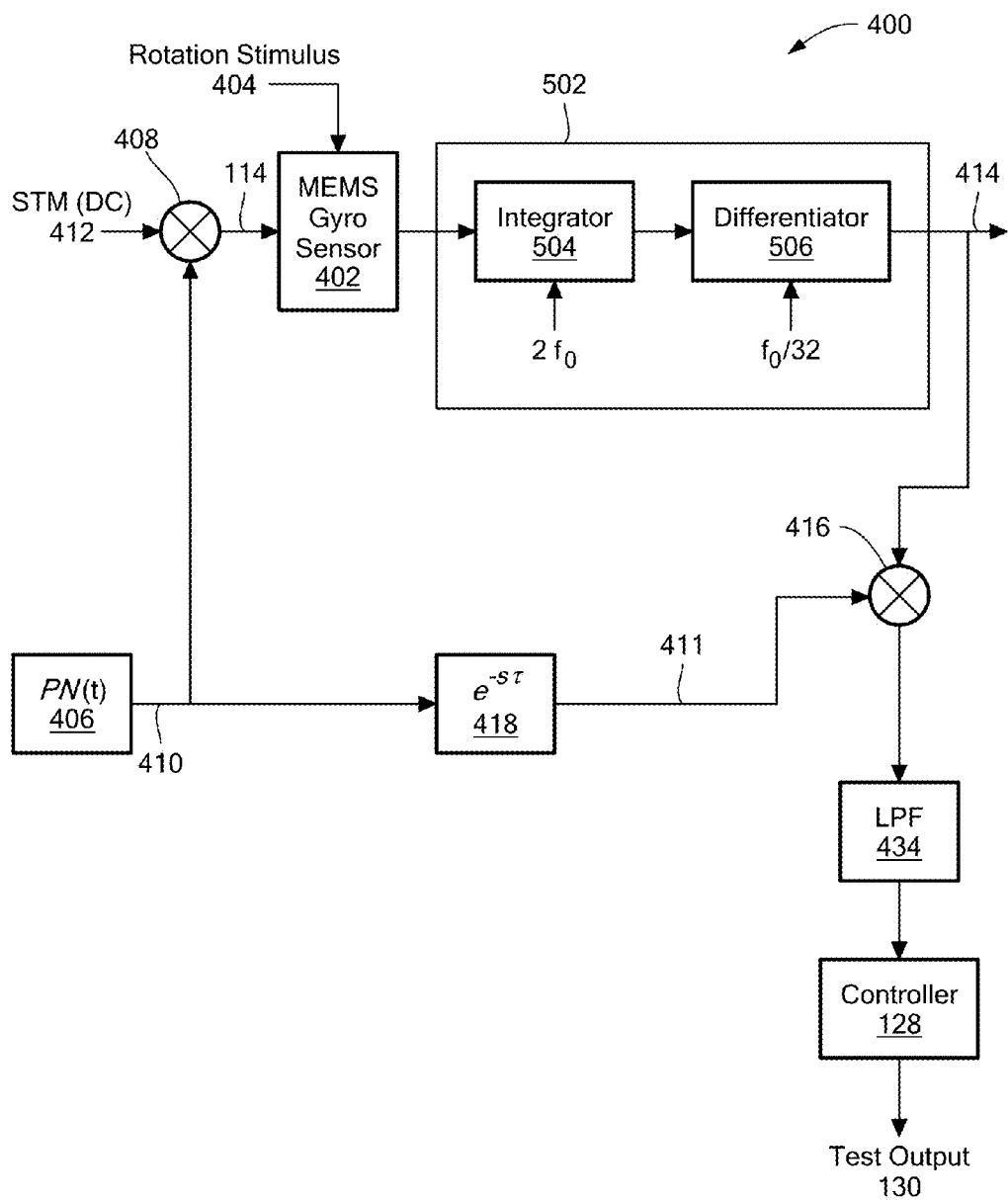
FIG. 5 schematically shows a MEMS system according to an embodiment.

FIG. 5 schematically shows a MEMS system according to an illustrative embodiment. The MEMS gyroscope sensor 402 may have an operating frequency ($f_0$) of 72 KHz, such as the MEMS gyroscope series no. ADxrs290 designed by Analog Devices, Inc. The bandwidth of the band pass filter may be specified as center frequency $f_0/16$, thus the pass band is between 69.75 KHz and 74.25 KHz where $f_0$−2.25 KHz<$B_{freq}$<$f_0$+2.25 KHz. The chipping frequency of the pseudo-random number generator may be 2.25 KHz (i.e., $f_0/32$). Here, the self-test signal detection portion may employ a cascade filter 502, such as a cascaded integrator-comb filter (CIC). The cascade filter 502 may have an integrator 504 and a differentiator 506. The integrator 504 may operate at sampling rate 2*$f_0$ and the differentiator 506 may operate at $f_0/32$.

Generally, cascade filters have a series of chained filters that may be coupled with rate changers (i.e., decimators and interpolators). Cascade filters may employ decimation techniques to allow for a shorter length number sequence (n). As such, simpler circuit implementation may be designed. For example, for a signal test signal having 1 deg/s and a rate of 30 deg/s, the power may be $\frac{1}{30}^{th}$ the magnitude of the Coriolis effect (i.e., 20 $\log_{10}(30)$=29.5). Accordingly, where a sequence of n>1023 may originally be necessary, the addition of a third-order low-pass filter with decimation may allow a length n=127 to be used. The third-order low pass filter may be implemented, for example, as a CIC low-pass filter of 127 and 255 taps.

Compared to self-test circuits known in the art, the implementation of a self-test circuit that measures the self-test stimulus with a multiplier, a delay circuit, and a third-order low pass filter may provide a smaller die footprint. Additionally, the components may have less stringent requirements (e.g., filter order, cut-off frequency and Q-factor) as compared to such known self-test circuits.

Figure 6:
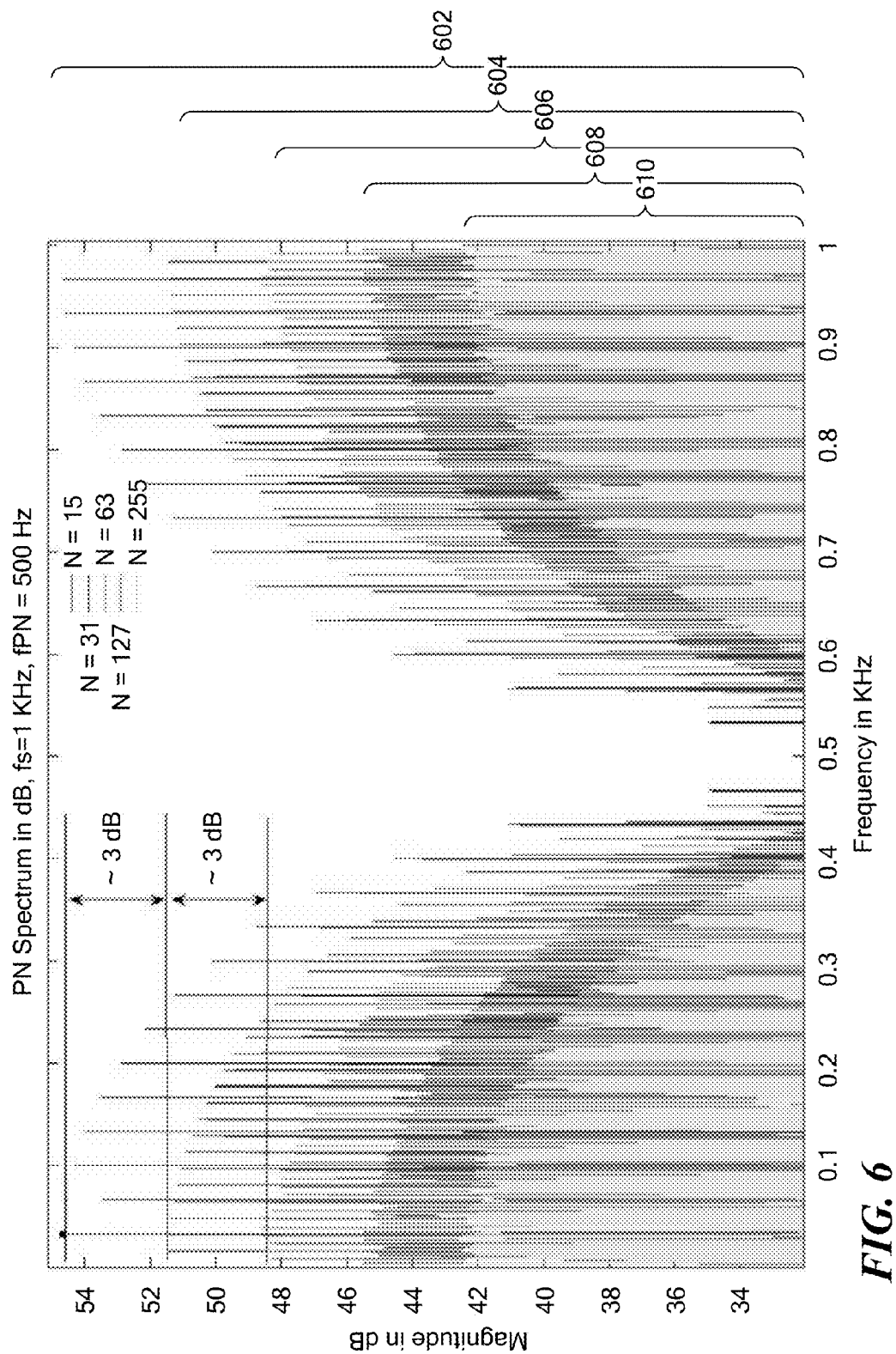
FIG. 6 is a plot illustrating the effect on spectrum power of varying length of the number sequence used to spread the self-test signal.

FIG. 6 is a plot illustrating the effect on spectrum power of varying length of the number sequence used to spread the self-test signal. Here, five power spectrums are shown, including 4-bit LFSR (i.e., N=14 sequence) 602, 5-bit LFSR (i.e., N=31 sequence) 604, 6-bit LFSR (i.e., N=63 sequence) 606, 7-bit (i.e., N=127 sequence) 608, and 8-bit (i.e., N=255 sequence) 610. As shown, with each additional bit to the sequence, the power spectrum spreads twice as much, thus the spread has a lower frequency component of approximately 3 dB (decibels). Thus, the length of the number sequence may be configured to produce a specific frequency component magnitude.

Figure 7:
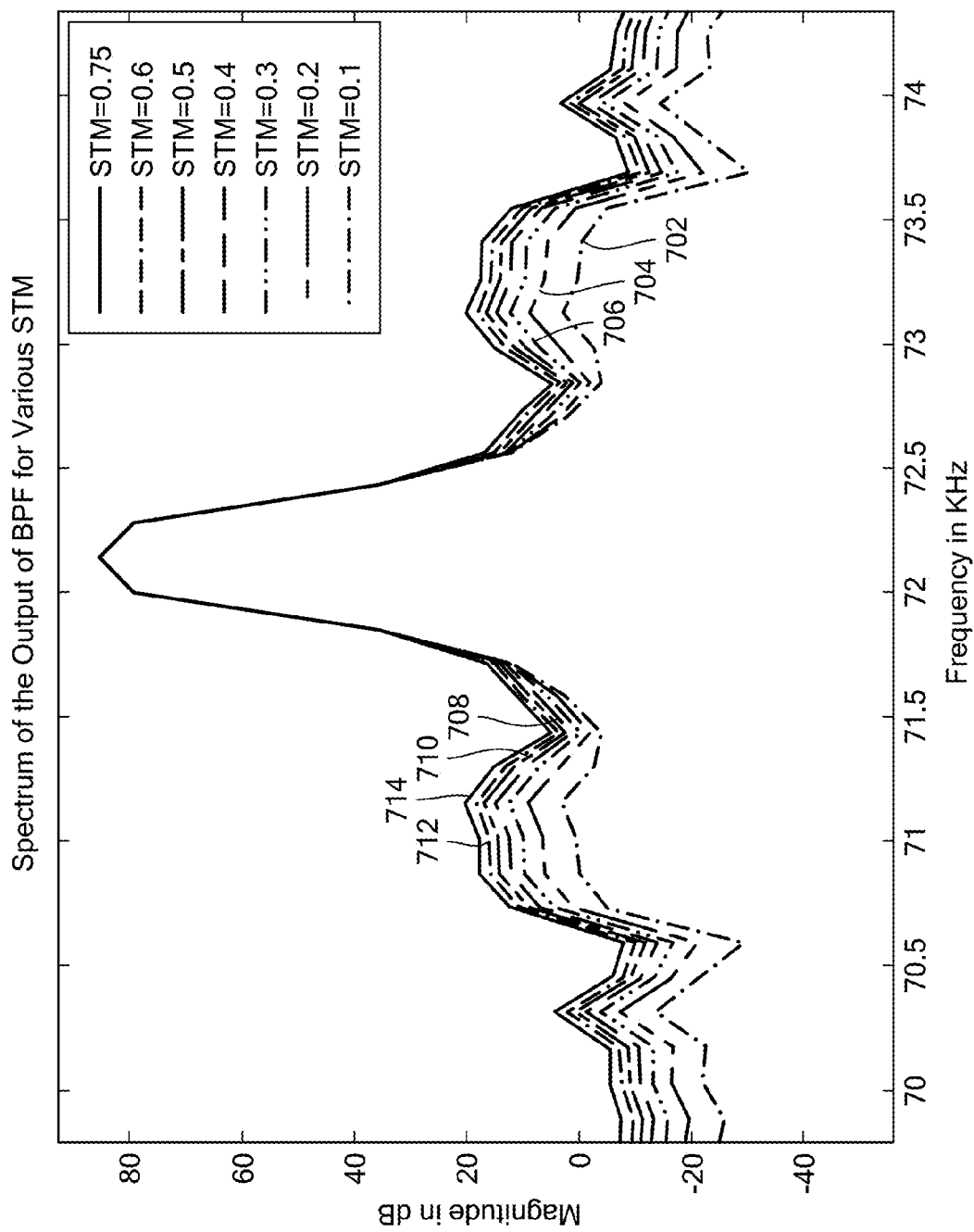
FIG. 7 is a plot illustrating the effect of the magnitude of the self-test signal on the power spectrum of the pseudo-random number generator.

FIG. 7 is a plot illustrating the effect of the magnitude of the self-test signal on the power spectrum of the pseudo-random number generator. Here, the x-axis shows a frequency range from 69.5 KHz to 74.5 KHz and the y-axis shows a magnitude of the power spectrum. The figure shows power spectrum of the output of the band-pass filter (Hann windowed) for various values of magnitude levels of the self-test signal, including "0.1" 702, "0.2" 704, "0.3" 706, "0.4" 708, "0.5" 710, "0.6" 712, and "0.75" 714. A value of "0.1" corresponds, for example, to the self-test signal being 10% of magnitude of the stimulus 104.

From the plot, if the amplitude of a sinusoidal signal is changed by a factor of two, power changes by a factor of four. Power is a log function, where 20*log 10|FFT| peak will produce a change of 6 dB. Similarly when the STM increases by a factor of two, the FFT peaks of the self-test signal 114 (e.g., PN sequence*STM) increases so that the overall power quadruples. When the amplitude is changed by a factor of three, it is observed that the resulting change in power is 9.5 dB. Here, the pseudo-random number has a sequence where N=31 and chipping frequency $f_c$=2.25 KHz. It is noted that a decrease in the self-test magnitude by half results in a FFT-magnitude reduction by a factor of four. As indicated, total power in the signal is proportional to $\Sigma|FFT|^2$.

Table 2 illustrates an effect of different self-test magnitude on self-test response. As observe, the resulting response may be higher or lower than the input magnitude of the self-test signal. The coriolis rate may be modeled as a, rate=bias+A*sin($2\pi ft$). Here, a bias of 30 deg/s is assumed and a stimulus of interest (A) input of zero.

TABLE 2

Effect of self-test signal magnitude on Self-test response

| S. No | STM (deg/s) | Coriolis rate = Bias + A * sin(2 * pi * f * t), f = 100 Hz | | STM recovered (deg/s) |
|---|---|---|---|---|
| | | Bias (deg/s) | A (deg/s) | |
| 1 | 0.5 | 30 | 0 | 0.6 |
| 2 | 1 | 30 | 0 | 0.95 |
| 3 | 2 | 30 | 0 | 1.66 |

Figure 8:
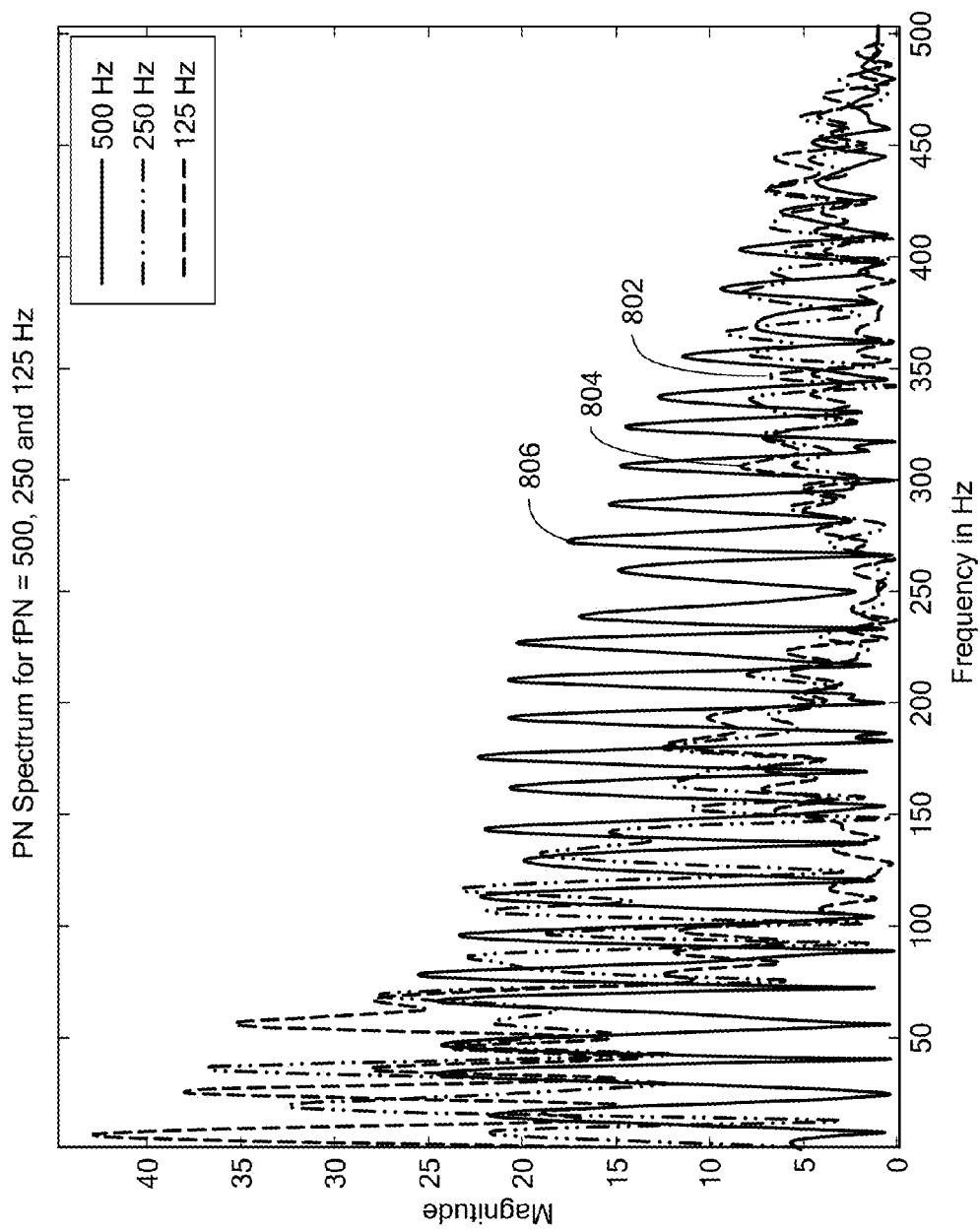
FIG. 8 is a plot illustrating the effect of the chipping frequency on the pseudo-random number generated sequence.

FIG. 8 is a plot illustrating the effect of the chipping frequency, $f_c$, on the pseudo-random number generated sequence. Here, the x-axis shows a frequency range from 0 to 500 Hz and the y-axis shows a magnitude of the power spectrum between 0 and 50. The pseudo-random number has a sequence where N=31 and chipping frequency $f_c$=125 Hz (802), 250 Hz (804), and 500 Hz (806).

Figure 9:
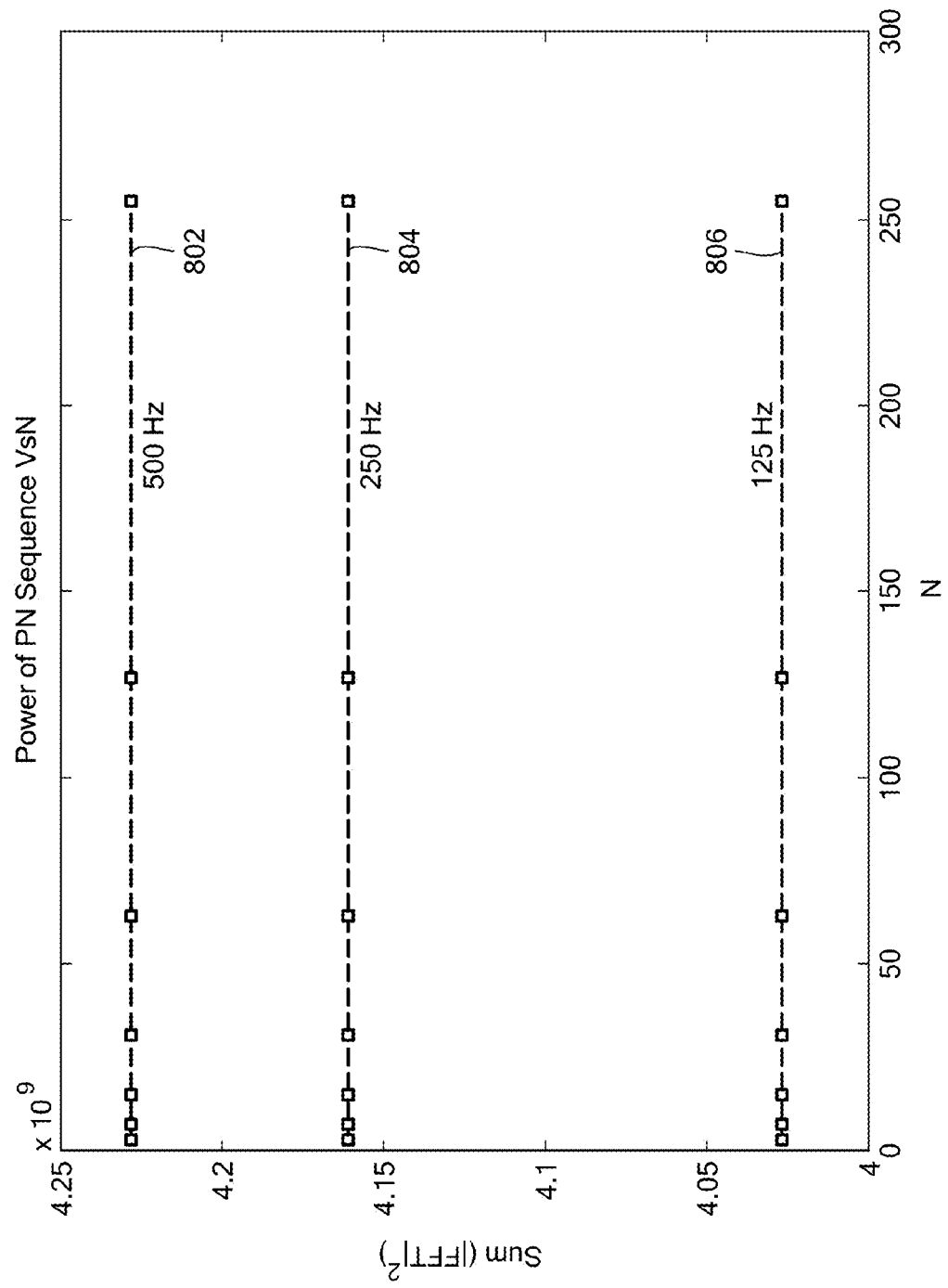
FIG. 9 is a plot illustrating the power of the spectrum of the pseudo-random number generated sequence of FIG. 8.

FIG. 9 is a plot illustrating the power of the spectrum of the pseudo-random number generated sequence of FIG. 8. It is observed that the power remains the same over N for the same chipping frequency ($f_c$).

Figure 10A:
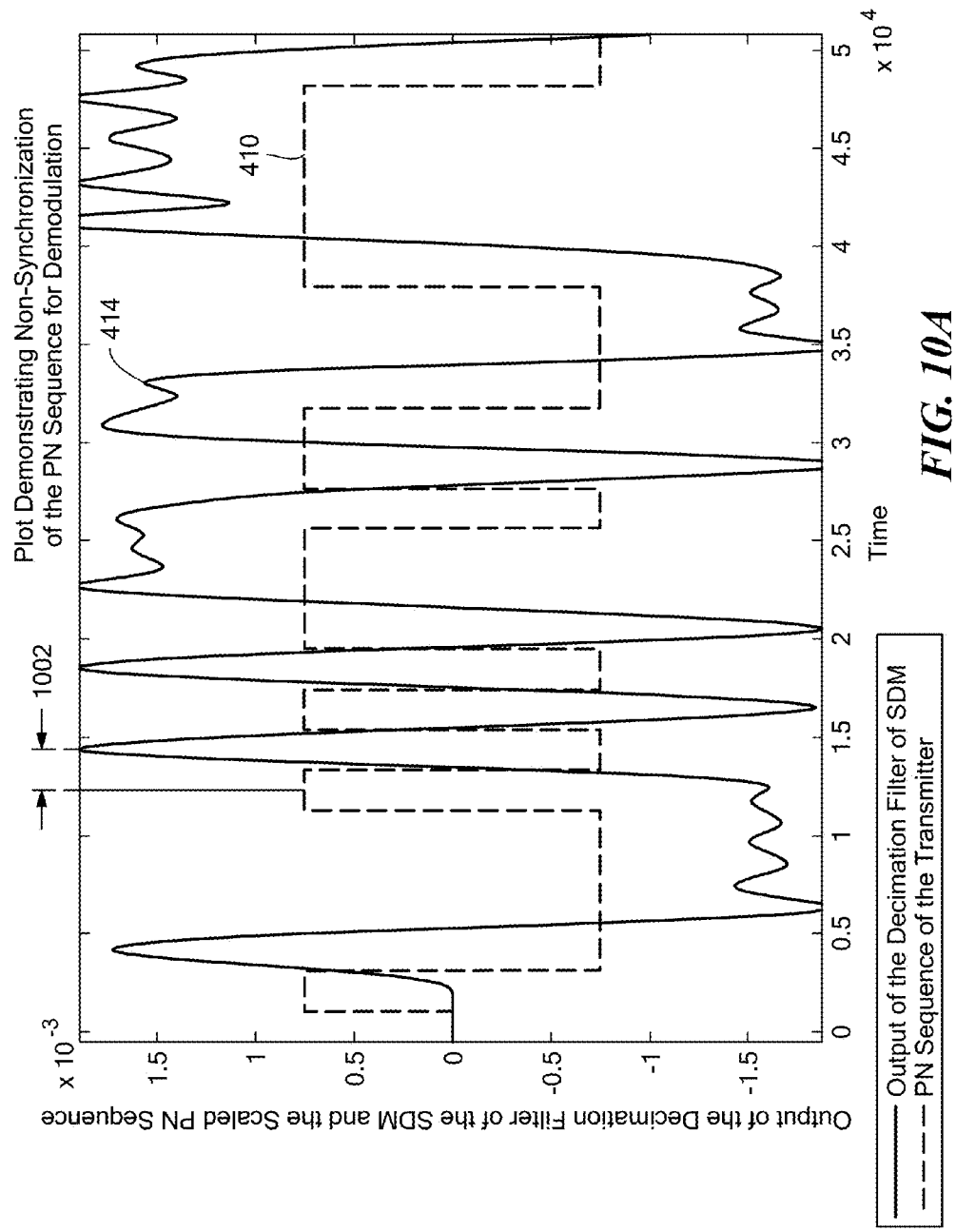
FIGS. 10A-B illustrate plots of the synchronization of the varying frequency self-test signal at the receiver.
Figure 10B:
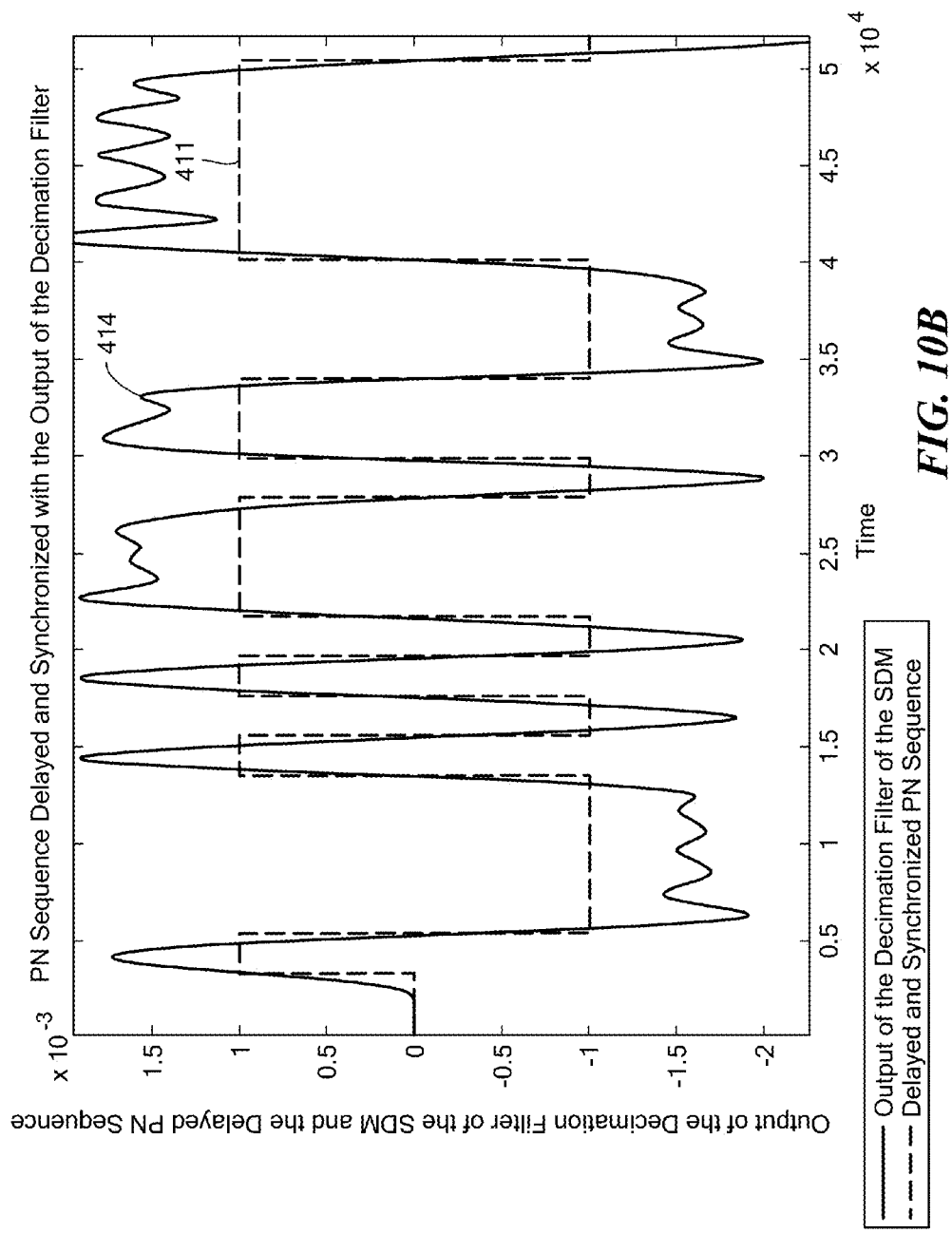

FIGS. 10A-B illustrate plots of the synchronization of the varying-frequency self-test signal at the receiver. FIG. 10A shows a time domain output of the output signal 414 and the pseudo-random number sequence 410. As shown, there exists a time offset 1002.

FIG. 10B shows a time-domain output of the output signal 414 and the in-phase pseudo-random number sequence 411. Here, the pseudo-random number sequence is delayed by 0.4558 ms. Any of various types of phase synchronization techniques may be employed, including, for example, phase-lock loops or correlation filters. The phase synchronization may be fixed, varying, or adaptive.

Figure 11:
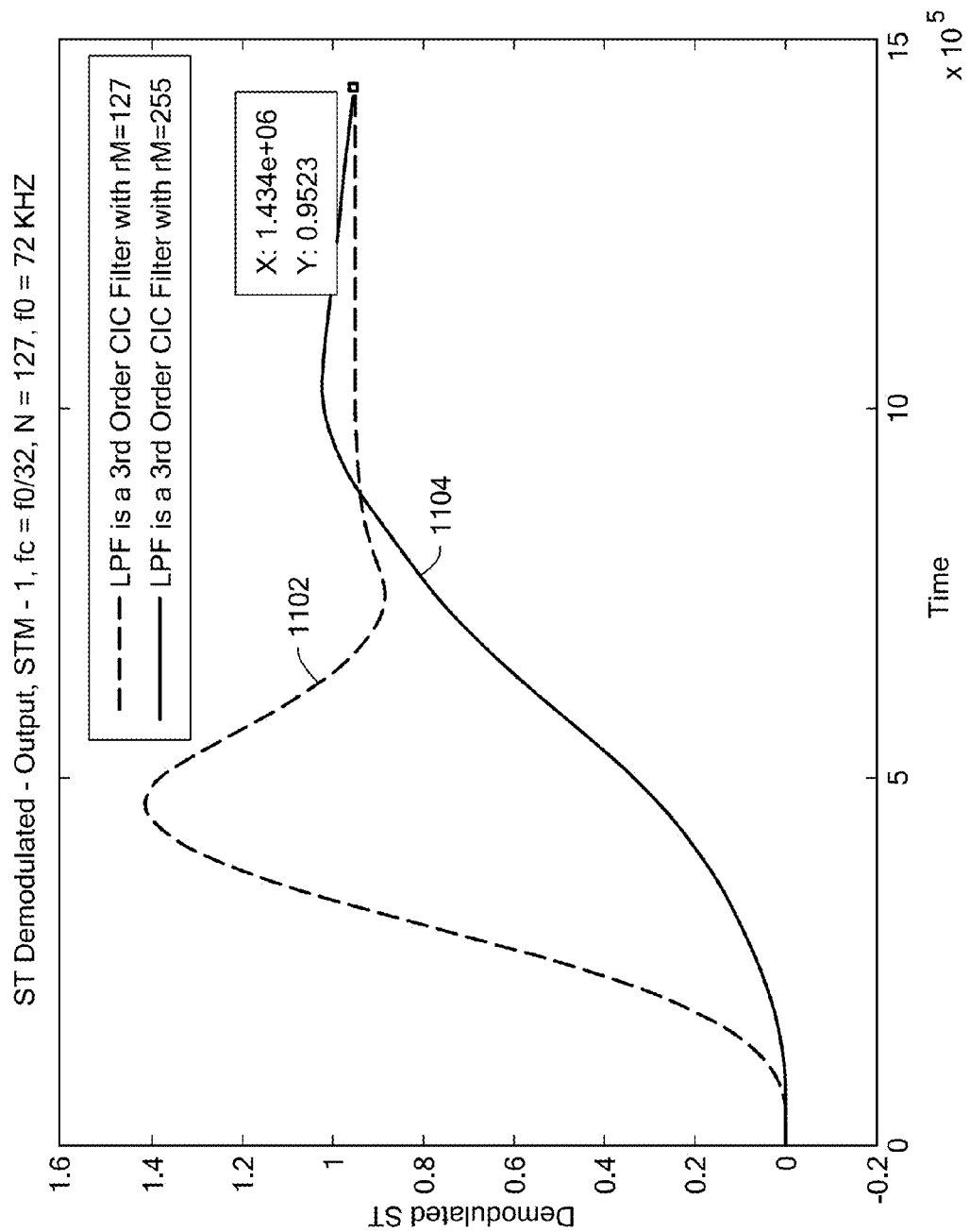
FIG. 11 is a plot of an output of a low-pass filter with different tap configuration.

FIG. 11 is a plot of an output of a low-pass filter with different tap configuration. Here, the final demodulated self-test response at the output of LPF is a constant close to 1 deg/s. The line 1102 shows the output for a third-order CIC filter with 127 taps (rM). The line 1104 shows the output for a third-order CIC filter with 255 taps (rM).

Figure 12:
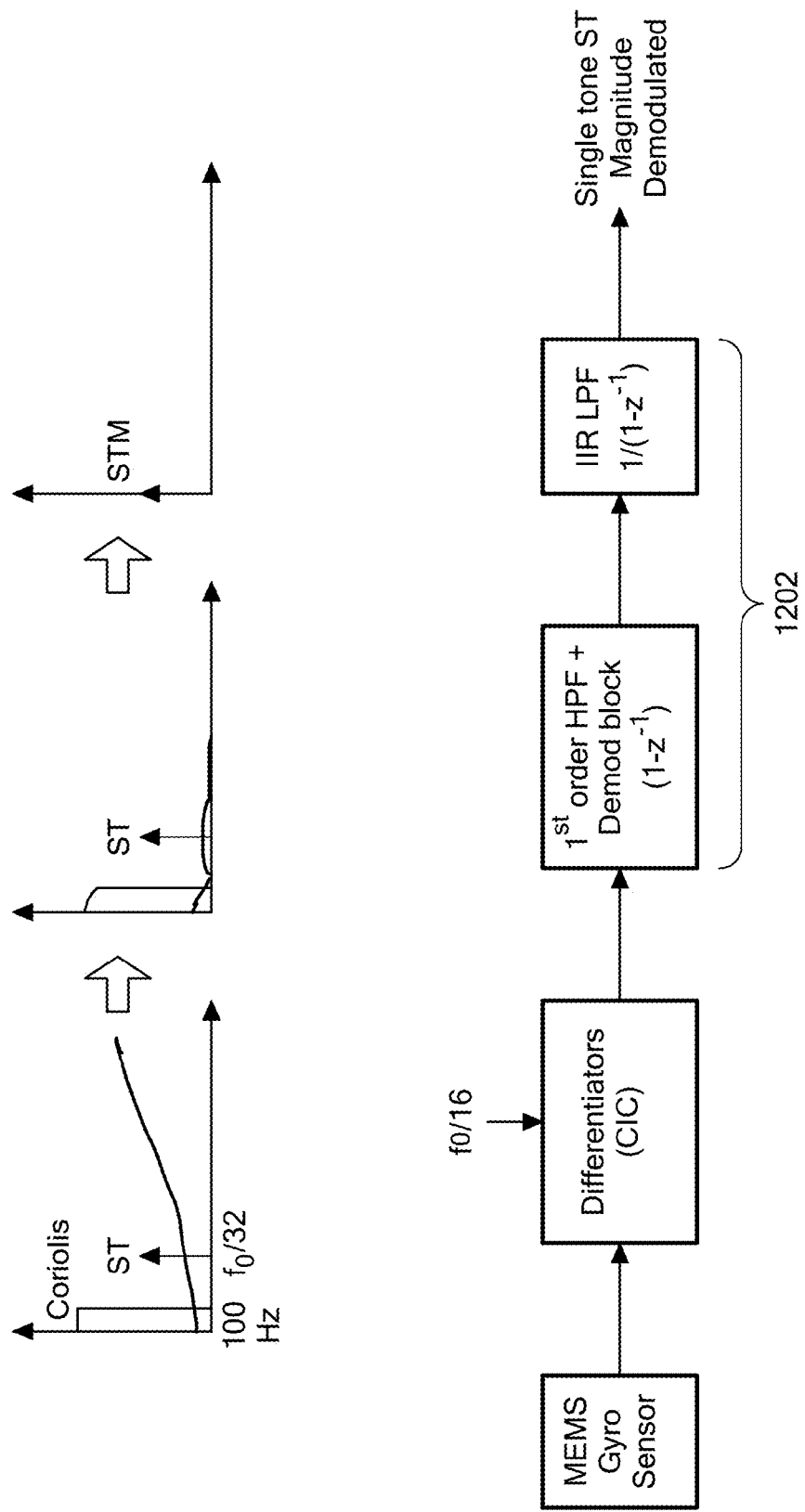
FIG. 12 schematically illustrates an example of a MEMS sensor with self-test capabilities as known in the art.

FIG. 12 schematically illustrates an example of a MEMS sensor with self-test capabilities as known in the art. As indicated, a self-test stimulus may be a periodic single tone signal (e.g., a sinusoid). Since a MEMS gyroscope also senses rotation simultaneously, the sensor output has two components, one due to rotation and the other due to self-test stimulus. The self-test component is separated from rotation component and is monitored continuously. Separating the single tone self-test from the baseband rotation rate signal may be implemented using a band pass filtering 1202. To separate the rotation rate (stimulus) from the self-test (self-test stimulus), multi-stage low pass filtering may need to be performed. This low pass filter should have a notch at a specific point where the single tone self-test resides. Thus, at least one BPF is in the self-test path, and at least one LPF is in the self-test path. This design has certain practical difficulties in the design, such as stringent filtering requirements to separate the self-test component (self-test stimulus) from the rotation rate component (stimulus), as well as vague criteria for the choice of an appropriate single tone frequency. Additionally, the usable sensor bandwidth for measuring the rotation rate (stimulus) is trade-off with the self-test stimulus, thus taking away from the effective measurable bandwidth of the sensor.

Figure 13:
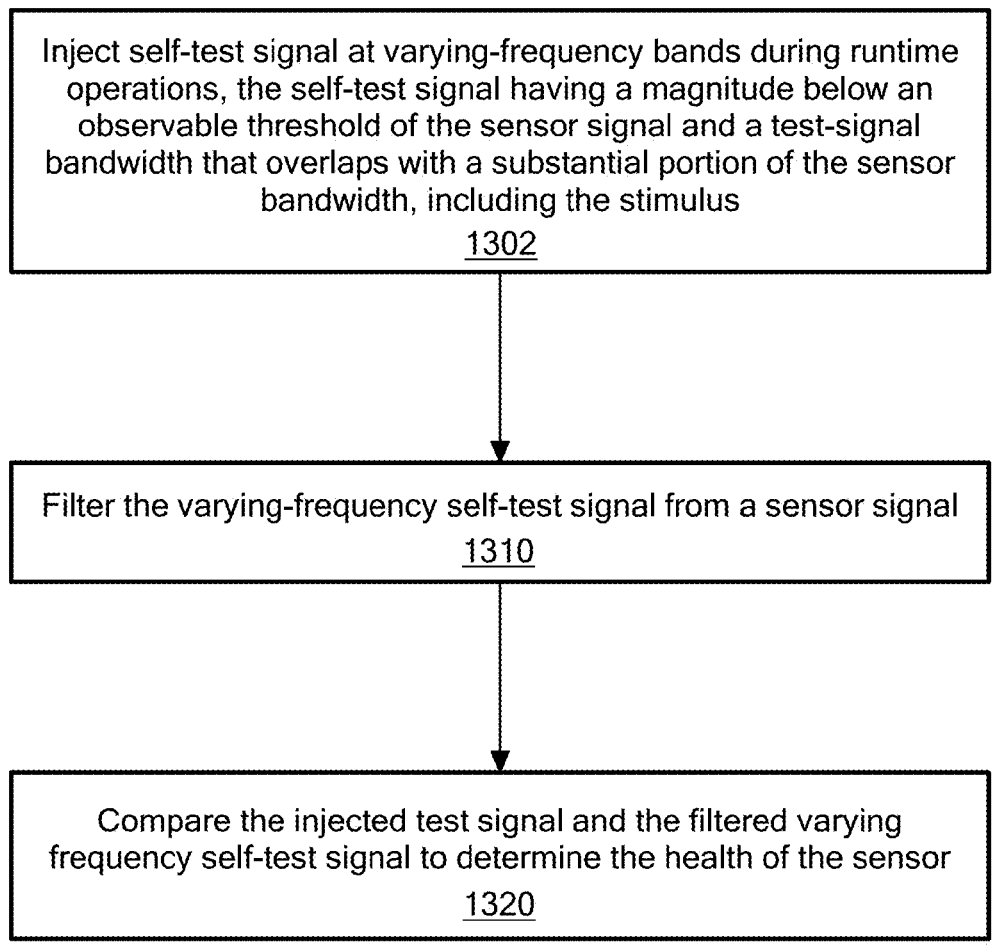
FIG. 13 is a flow chart of a method according to an illustrative embodiment.

FIG. 13 is a flow chart of a method according to the illustrative embodiment. A self-test signal having varying-frequency bands is injected into a MEMS sensor (step 1302. The varying frequency self-test signal is filtered from a sensor signal from the MEMS sensor (step 1310). The injected self-test signal is compared to the filtered varying frequency self-test signal to determine the health of the MEMS sensor (step 1320).

The self-test operation may be initialized as the MEMS sensor is initialized. Alternatively, the self-test operation may operate independently of the MEMS sensor operation. For example, the MEMS sensor may be configured with a test mode in which the self-test signal may be solely injected into the MEMS sensor.

It should be apparent to one skilled in the art that the various embodiments may be applied to other types of MEMS sensors, including, for example, accelerometers, microphones, and pressure sensors.

It should be noted that arrows may be used in drawings to represent communication, transfer, or other activity involving two or more entities. Double-ended arrows generally indicate that activity may occur in both directions (e.g., a command/request in one direction with a corresponding reply back in the other direction, or peer-to-peer communications initiated by either entity), although in some situations, activity may not necessarily occur in both directions. Single-ended arrows generally indicate activity exclusively or predominantly in one direction, although it should be noted that, in certain situations, such directional activity actually may involve activities in both directions (e.g., a message from a sender to a receiver and an acknowledgement back from the receiver to the sender, or establishment of a connection prior to a transfer and termination of the connection following the transfer). Thus, the type of arrow used in a particular drawing to represent a particular activity is exemplary and should not be seen as limiting.

It should also be noted that logic flows may be described herein to demonstrate various aspects of the invention, and should not be construed to limit the present invention to any particular logic flow or logic implementation. The described logic may be partitioned into different logic blocks (e.g., programs, modules, functions, or subroutines) without changing the overall results or otherwise departing from the true scope of the invention. Often times, logic elements may be added, modified, omitted, performed in a different order, or implemented using different logic constructs (e.g., logic gates, looping primitives, conditional logic, and other logic constructs) without changing the overall results or otherwise departing from the true scope of the invention.

Aspects of the present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof. Computer program logic implementing some or all of the described functionality is typically implemented as a set of computer program instructions that is converted into a computer executable form, stored as such in a computer readable medium, and executed by a microprocessor under the control of an operating system. Hardware-based logic implementing some or all of the described functionality may be implemented using one or more appropriately configured FPGAs. For example, the self-test circuits 112 and 212 may be implemented solely in hardware or may be implemented with a combination of hardware and software. The signal processing ASIC 304 is generally implemented solely in hardware.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

Computer program logic implementing all or part of the functionality previously described herein may be executed at different times on a single processor (e.g., concurrently) or may be executed at the same or different times on multiple processors and may run under a single operating system process/thread or under different operating system processes/threads. Thus, the term "computer process" refers generally to the execution of a set of computer program instructions regardless of whether different computer processes are executed on the same or different processors and regardless of whether different computer processes run under the same operating system process/thread or different operating system processes/threads.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web). Of course, some embodiments of the invention may be implemented as a combination of both software (e.g., a computer program product) and hardware. Still other embodiments of the invention are implemented as entirely hardware, or entirely software.

The present invention may be embodied in other specific forms without departing from the true scope of the invention, and numerous variations and modifications will be apparent to those skilled in the art based on the teachings herein. Any references to the "invention" are intended to refer to exemplary embodiments of the invention and should not be construed to refer to all embodiments of the invention unless the context otherwise requires. The described embodiments are to be considered in all respects only as illustrative and not restrictive.

What is claimed is:

1. A MEMS sensor having a runtime self-test circuit, the MEMS sensor comprising:
   a micro-electromechanical device that outputs, during runtime operation, a device output signal;
   a detection circuit configured to detect, during the runtime operation of the micro-electromechanical device, a stimulus produced by the micro-electromechanical system in a sensor bandwidth of the device output signal, the stimulus having a magnitude above a predetermined detection threshold of the detection circuit, the detection circuit further configured to produce a sensor output signal based on the detected stimulus; and
   a self-test circuit configured to:
   inject, during the runtime operation of the micro-electromechanical device, a self-test signal into a signal path of the micro-electromechanical device including a MEMS structure involved with generation of the stimulus in the sensor bandwidth of the device output signal, wherein the self-test signal is a spread-spectrum signal having a test-signal bandwidth that overlaps at least a portion of the sensor bandwidth;
   detect a test signal component in the test-signal bandwidth of the device output signal based on a reference test signal corresponding to the injected self-test signal, the test signal component have a magnitude below the detection threshold of the detection circuit; and
   produce a test output signal indicating a status for the micro-electromechanical system based on the test signal component and the reference test signal.

2. A MEMS sensor according to claim 1, wherein the self-test circuit is configured to continuously inject the self-test signal into the micro-electromechanical device during the runtime operation of the micro-electromechanical device.

3. A MEMS sensor according to claim 1, wherein the self-test circuit comprises:
   a pseudo-random number sequence source configured to provide a pseudo-random number sequence; and
   a modulation circuit configured to modulate the pseudo-random number sequence and a self-test magnitude reference to produce a modulated signal and to inject the modulated signal into the micro-electromechanical device.

4. A MEMS sensor according to claim 3, wherein at least one of:
   the self-test magnitude reference is a constant direct-current (DC) source;
   the pseudo-random number sequence source comprises a pseudo-random number generator;
   the pseudo-random number sequence source comprises a memory in which is stored the pseudo-random number sequence;
   the bandwidth of the self-test signal is equal to the sensor bandwidth;
   the bandwidth of the self-test signal is less than the sensor bandwidth;
   the bandwidth of the self-test signal is greater than the sensor bandwidth;
   the bandwidth of the self-test signal extends below the sensor bandwidth; or
   the bandwidth of the self-test signal extends above the sensor bandwidth.

5. A MEMS sensor according to claim 3, wherein the self-test circuit further comprises:
   a demodulation circuit configured to detect the test signal component by demodulating the device output signal with the reference test signal in-phase with test signal component.

6. A MEMS sensor according to claim 5, wherein at least one of:
   the self-test circuit further comprises a low-pass filter to extract the test signal component from the device output signal;
   the self-test circuit further comprises a delay circuit to produce the reference test signal in-phase with the test signal component;
   the self-test circuit further comprises a memory to provide the reference test signal; or
   the demodulation circuit comprises a multiplier to combine the test signal component with the in-phase reference test signal.

7. A MEMS sensor according to claim 1, wherein the self-test circuit is configured to detect the test signal component in the test-signal bandwidth of the device output by:

(i) correlating the sensor signal with the pseudo-random number sequence in phase with the sensor signal to produce a correlation signal; and (ii) comparing the correlation signal to at least one of a pre-defined correlation threshold or a pre-defined signal energy threshold.

8. A MEMS sensor according to claim 7, wherein the pre-defined energy threshold is established based on the relationship:

$$fc * STM^2$$

wherein fc is a frequency value of the injected self-test test signal and STM is an average power of a period spread of the injected self-test signal.

9. A MEMS sensor according to claim 1, wherein the self-test circuit is configured to inject the self-test signal according to at least one of a frequency-hopping spread spectrum modulation, a direct-sequence spread spectrum (DSSS) modulation, a time-hopping spread spectrum modulation, or a chirp spread spectrum modulation.

10. A MEMS sensor according to claim 1, wherein the micro-electromechanical device includes at least one of:
an inertial sensor;
a sound sensor; or
a pressure sensor.

11. A self-test circuit for a micro-electromechanical system that outputs, during runtime operation, a device output signal including a stimulus in a sensor bandwidth of the device output signal, the stimulus having a magnitude above a predetermined detection threshold, the self-test circuit comprising:
a self-test signal generator configured to inject, during runtime operation of the micro-electromechanical device, a self-test signal into a signal path of the micro-electromechanical device including a MEMS structure involved with generation of the stimulus in a sensor bandwidth of the device output signal, wherein the self-test signal is a spread-spectrum signal having a test-signal bandwidth that overlaps at least a portion of the sensor bandwidth;
a self-test signal detector configured to detect a test signal component in the test-signal bandwidth of the device output signal based on a reference test signal corresponding to the injected self-test signal, the test signal component have a magnitude below the detection threshold of the detection circuit; and
a controller configured to produce a test output signal based on the detected test signal component.

12. A self-test circuit according to claim 11, wherein the self-test signal generator is configured to continuously inject the self-test signal into the micro-electromechanical device during the runtime operation of the micro-electromechanical device.

13. A self-test circuit according to claim 11, wherein the self-test signal generator comprises:
a pseudo-random number sequence source configured to provide a pseudo-random number sequence; and
a modulation circuit configured to modulate the pseudo-random number sequence and a self-test magnitude reference to produce a modulated signal and to inject the modulated signal into the micro-electromechanical device.

14. A self-test circuit according to claim 13, wherein at least one of:
the self-test magnitude reference is a constant direct-current (DC) source;
the pseudo-random number sequence source comprises a pseudo-random number generator;
the pseudo-random number sequence source comprises a memory in which is stored the pseudo-random number sequence;
the bandwidth of the self-test signal is equal to the sensor bandwidth;
the bandwidth of the self-test signal is less than the sensor bandwidth;
the bandwidth of the self-test signal is greater than the sensor bandwidth;
the bandwidth of the self-test signal extends below the sensor bandwidth; or
the bandwidth of the self-test signal extends above the sensor bandwidth.

15. A self-test circuit according to claim 11, wherein the self-test signal detector comprises:
a demodulation circuit configured to detect the test signal component by demodulating the device output signal with the reference test signal in-phase with test signal component.

16. A self-test circuit according to claim 15, wherein at least one of:
the self-test signal detector comprises a low-pass filter to extract the test signal component from the device output signal;
the self-test signal detector comprises a delay circuit to produce the reference test signal in-phase with the test signal component;
the self-test signal detector comprises a memory to provide the reference test signal; or
the demodulation circuit comprises a multiplier to combine the test signal component with the in-phase reference test signal.

17. A self-test circuit according to claim 11, wherein the self-test signal detector is configured to detect the test signal component in the test-signal bandwidth of the device output by:
(i) correlating the sensor signal with the pseudo-random number sequence in phase with the sensor signal to produce a correlation signal; and
(ii) comparing the correlation signal to at least one of a pre-defined correlation threshold or a pre-defined signal energy threshold.

18. A self-test circuit according to claim 17, wherein the pre-defined energy threshold is established based on the relationship:

$$fc * STM^2$$

wherein fc is a frequency value of the injected self-test test signal and STM is an average power of a period spread of the injected self-test signal.

19. A self-test circuit according to claim 11, wherein the self-test circuit is configured to inject the self-test signal according to at least one of a frequency-hopping spread spectrum modulation, a direct-sequence spread spectrum (DSSS) modulation, a time-hopping spread spectrum modulation, or a chirp spread spectrum modulation.

20. A method of evaluating the status of a MEMS sensor during runtime, the MEMS sensor having a micro-electromechanical device that outputs, during a runtime operation, a device output signal, the MEMS sensor further having a detection circuit configured to detect, during the runtime operation of the micro-electromechanical device, a stimulus produced by the micro-electromechanical system in a sensor bandwidth of the device output signal, the stimulus having a magnitude above a predetermined detection threshold of the detection circuit, the detection circuit further configured to produce a sensor output signal based on the detected stimulus, the method comprising:

injecting, during runtime operation of the micro-electromechanical device, a self-test signal into a signal path of the micro-electromechanical device including a MEMS structure involved with generation of a stimulus in a sensor bandwidth of a device output signal, wherein the self-test signal is a spread-spectrum signal having a test-signal bandwidth that overlaps at least a portion of the sensor bandwidth;

detecting a test signal component in the test-signal bandwidth of the device output signal based on a reference test signal corresponding to the injected self-test signal, the test signal component have a magnitude below the detection threshold of the detection circuit; and producing a test output signal based on the detected test signal component.

\* \* \* \* \*